(12) United States Patent
Wada et al.

(10) Patent No.: US 8,487,048 B2
(45) Date of Patent: Jul. 16, 2013

(54) WATER-ABSORBENT RESIN AND ITS PRODUCTION PROCESS

(75) Inventors: Katsuyuki Wada, Himeji (JP); Masatoshi Nakamura, Himeji (JP); Kazuki Kimura, Himeji (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 688 days.

(21) Appl. No.: 10/555,707

(22) PCT Filed: May 7, 2004

(86) PCT No.: PCT/JP2004/006509
§ 371 (c)(1),
(2), (4) Date: Nov. 3, 2005

(87) PCT Pub. No.: WO2004/099265
PCT Pub. Date: Nov. 18, 2004

(65) Prior Publication Data
US 2006/0276598 A1 Dec. 7, 2006

(30) Foreign Application Priority Data

May 9, 2003 (JP) ................................. 2003-132204

(51) Int. Cl.
*C08F 8/00* (2006.01)
*C08F 8/14* (2006.01)
*C08F 8/32* (2006.01)
*A61F 13/53* (2006.01)

(52) U.S. Cl.
USPC .................. 525/330.2; 525/329.7; 525/330.1; 525/329.9; 525/379; 525/381; 525/382; 525/384; 524/556; 428/327; 526/317.1; 526/318.5

(58) Field of Classification Search
USPC ............. 525/329.7, 330.1, 330.2, 329.9, 379, 525/381, 382, 384; 524/556; 428/327; 526/317.1, 318.5
See application file for complete search history.

(56) References Cited

U.S. PATENT DOCUMENTS

| | | |
|---|---|---|
| RE32,649 E | 4/1988 | Brandt et al. |
| 5,051,259 A | 9/1991 | Olsen et al. |
| 5,140,076 A | 8/1992 | Hatsuda et al. |
| 5,147,343 A | 9/1992 | Kellenberger |
| 5,149,335 A | 9/1992 | Kellenberger et al. |
| 5,419,956 A | 5/1995 | Roe |
| 5,453,323 A | 9/1995 | Chambers et al. |
| 5,462,972 A | 10/1995 | Smith et al. |
| 5,562,646 A | 10/1996 | Goldman et al. |
| 5,601,542 A | 2/1997 | Melius et al. |
| 5,610,220 A | 3/1997 | Klimmek et al. |
| 5,669,894 A | 9/1997 | Goldman et al. |
| 5,672,633 A | 9/1997 | Brehm et al. |
| 5,712,316 A | 1/1998 | Dahmen et al. |
| 5,760,080 A | 6/1998 | Wada et al. |
| 5,797,893 A | 8/1998 | Wada et al. |
| 5,866,678 A | 2/1999 | Kajikawa et al. |
| 5,994,440 A | 11/1999 | Staples et al. |
| 6,087,002 A | 7/2000 | Kimura et al. |
| 6,127,454 A | 10/2000 | Wada et al. |
| 6,150,582 A | 11/2000 | Wada et al. |
| RE37,021 E | 1/2001 | Aida |
| 6,184,433 B1 * | 2/2001 | Harada et al. .................. 604/372 |
| 6,194,531 B1 | 2/2001 | Hatsuda et al. |
| 6,254,990 B1 | 7/2001 | Ishizaki et al. |
| 6,265,488 B1 * | 7/2001 | Fujino et al. ................... 525/119 |
| 6,297,335 B1 | 10/2001 | Funk et al. |
| 6,414,214 B1 | 7/2002 | Engelhardt et al. |
| 6,444,744 B1 | 9/2002 | Fujimaru et al. |
| 6,562,879 B1 * | 5/2003 | Hatsuda et al. .................. 521/56 |
| 6,599,989 B2 | 7/2003 | Wada et al. |
| 6,617,489 B2 | 9/2003 | Wada et al. |
| 6,817,557 B2 | 11/2004 | Kakita et al. |
| 6,849,665 B2 | 2/2005 | Frenz et al. |
| 7,872,076 B2 * | 1/2011 | Ikeuchi et al. ............. 525/329.7 |
| 7,981,833 B2 * | 7/2011 | Ikeuchi et al. ................ 502/402 |

(Continued)

FOREIGN PATENT DOCUMENTS

| | | |
|---|---|---|
| DE | 100 16 041 | 10/2001 |
| EP | 0 780 424 | 6/1997 |
| EP | 0 885 917 | 12/1998 |
| EP | 1 153 656 | 11/2001 |
| EP | 1153656 A2 * | 11/2001 |
| EP | 1 191 051 | 3/2002 |
| JP | 61-48521 | 10/1986 |
| JP | 1-132802 | 5/1989 |

(Continued)

*Primary Examiner* — Roberto Robago
(74) *Attorney, Agent, or Firm* — Roylance, Abrams, Berdo & Goodman, L.L.P.

(57) ABSTRACT

Objects of the present invention are: to provide a water-absorbent resin which exhibits excellent balances between water absorption performances; and further to provide a process by which a water-absorbent resin having excellent absorption properties can be produced even if no hydrophilic organic solvent is used, or even if its amount is extremely reduced, when carrying out the surface-crosslinking treatment; and further to provide a water-absorbent resin optimum to absorbent articles such as diapers. As a means of achieving these objects, the process according to the present invention for production of the water-absorbent resin comprises: a step (1) of polymerizing a monomer component including an acid-group-containing unsaturated monomer as an essential component to thereby obtain a hydrogel polymer; a step (2) of drying and pulverizing the hydrogel polymer to thereby obtain a water-absorbent resin powder; a step (3) of adding a surface-crosslink-treating agent to the water-absorbent resin powder, wherein the surface-crosslink-treating agent includes a surface-crosslinking agent and water as essential components and has a hydrophilic organic solvent content of 0 to 10 mass % relative to the surface-crosslink-treating agent; and a step (4) of heating the resultant mixture to thereby carry out surface-crosslinking treatment; wherein a time of from the end of the step (3) till the beginning of the step (4) is within 5 minutes.

32 Claims, No Drawings

U.S. PATENT DOCUMENTS

| | | | |
|---|---|---|---|
| 2002/0040095 A1* | 4/2002 | Dairoku et al. | 524/832 |
| 2002/0120085 A1* | 8/2002 | Matsumoto et al. | 526/317.1 |
| 2003/0065087 A1* | 4/2003 | Nambu et al. | 524/588 |
| 2003/0087983 A1* | 5/2003 | Kajikawa et al. | 522/150 |
| 2004/0071966 A1 | 4/2004 | Inger et al. | |
| 2005/0288182 A1* | 12/2005 | Torii et al. | 502/402 |

FOREIGN PATENT DOCUMENTS

| | | |
|---|---|---|
| JP | 04-246403 | 9/1992 |
| JP | 4-246403 | 9/1992 |
| JP | 07-059813 | 3/1995 |
| JP | 07-242709 | 9/1995 |
| JP | 8-508517 | 9/1996 |
| JP | 9-502221 | 3/1997 |
| JP | 11-060630 | 3/1999 |
| JP | 11-140194 | 5/1999 |
| JP | 11-349625 | * 12/1999 |
| JP | 2000-026510 | * 1/2000 |
| JP | 2001-270948 | 10/2001 |
| JP | 2002-121291 | 4/2002 |
| JP | 3305718 | 5/2002 |
| JP | 2003-529647 | 10/2003 |
| WO | WO 95/27739 | 10/1995 |
| WO | WO 01/74913 | 10/2001 |
| WO | WO 02/100451 | 12/2002 |
| WO | WO 03/004550 | * 1/2003 |
| WO | WO 2004/069936 | 8/2004 |

* cited by examiner

WATER-ABSORBENT RESIN AND ITS PRODUCTION PROCESS

TECHNICAL FIELD

The present invention relates to a water-absorbent resin and its production process. More specifically, the present invention relates to a water-absorbent resin having excellent performances and its production process which involves carrying out specific surface-crosslinking treatment.

BACKGROUND ART

In recent years, water-absorbent resins are widely used as component materials of sanitary materials (e.g. disposable diapers, sanitary napkins, incontinent pads) for the purpose of causing the water-absorbent resins to absorb aqueous liquids such as body fluids.

Known examples of the above water-absorbent resins include: partially-neutralized and crosslinked poly(acrylic acids); hydrolyzed copolymers of starch-acrylonitrile; neutralized graft polymers of starch-acrylic acid; saponified copolymers of vinyl acetate-acrylic acid ester; hydrolyzed copolymers of acrylonitrile or acrylamide, or crosslinked polymers of these hydrolyzed copolymers; crosslinked carboxymethyl cellulose; crosslinked copolymers of 2-acrylamido-2-methylpropanesulfonic acid (AMPS); crosslinked poly(ethylene oxide); crosslinked poly(allylamine); and crosslinked polyethylenimine.

Examples of properties, which the above water-absorbent resins should have, include excellent properties when contacting with aqueous liquids (e.g. body fluids), such as: water absorption quantity; absorption rate; liquid permeability; gel strength of swollen gel; and suction force to suck up water from base materials containing the aqueous liquids.

The relations between these properties do not necessarily show positive correlations. For example, there has been a tendency such that, as the absorption properties without load become higher, those under load unfavorably decrease.

Arts in which surface layers of the water-absorbent resins are crosslinked, which are called surface-crosslinking treatment arts, are known as processes for well-balanced improvement of the properties of the water-absorbent resins.

As crosslinking agents used for the surface-crosslinking treatment, there are known such as polyhydric alcohols, polyglycidyl ethers, haloepoxy compounds, polyaldehydes, polyamines, and polyvalent metal salts. As processes for crosslinking the surface layers of the water-absorbent resins with these crosslinking agents, there are known the following representative processes such as: a process in which a surface-crosslink-treating agent and the water-absorbent resin are mixed together and then heated, wherein the surface-crosslink-treating agent is prepared by dissolving the crosslinking agent into water and a hydrophilic organic solvent (e.g. refer to patent documents 1 to 3 below); and a process in which the water-absorbent resin is dispersed into a mixed solvent of water and the hydrophilic organic solvent, and then the crosslinking agent is added to the resultant dispersion to carry out their reaction (e.g. refer to patent document 4 below).

On the other hand, the surface-crosslinking treatment is desired to be carried out without any hydrophilic organic solvent, for example, from the viewpoint of: problems of environmental contamination due to waste liquids and/or waste gases discharged during the production; and use circumstances such that the water-absorbent resin is used for the sanitary materials which contact directly with human bodies. However, in the case where the water-absorbent resin is produced by using water as the only solvent without the hydrophilic organic solvent when carrying out the surface-crosslinking treatment (e.g. refer to patent document 5 below), then there have been problems in that the properties, particularly, absorption properties, of the water-absorbent resin are unfavorably deteriorated when compared with the case where the hydrophilic organic solvent is used.

Furthermore, hitherto, such as production conditions of the water-absorbent resins themselves and conditions of their surface treatment (as post-processing) have been studied, and many water-absorbent resins have been designed or produced with attention directed to the aforementioned properties (e.g. water absorption quantity, absorption rate, liquid permeability, gel strength, suction force). However, from the viewpoint of practical uses for absorption of excreta and blood (e.g. diapers), it has recently been being found that there is a case where the absorption performances cannot be exercised on the desired high levels by merely satisfying these properties. In other words, as to water-absorbent resins used in absorbent articles for absorption of excreta and blood, there have been problems in that the design or production of the optimum water-absorbent resin has not yet succeeded.

Patent Document 1

JP-A-270948/2001 (Kokai)

Patent Document 2

JP-A-502221/1997 (Kohyo)

Patent Document 3

Japanese Patent No. 3305718

Patent Document 4

JP-B-048521/1986 (Kokoku)

Patent Document 5

JP-A-246403/1992 (Kokai)

DISCLOSURE OF THE INVENTION

Objects of the Invention

Accordingly, objects of the present invention are: to provide a water-absorbent resin which exhibits excellent balances between water absorption performances; and further to provide a process by which a water-absorbent resin having excellent absorption properties can be produced even if no hydrophilic organic solvent is used, or even if its amount is extremely reduced, when carrying out the surface-crosslinking treatment in the process of producing the water-absorbent resin.

Another object of the present invention is to provide a water-absorbent resin optimum to absorbent articles such as diapers.

Summary of the Invention

The present inventors diligently studied to solve the above problems. As a result, the present inventors directed their attention to an intermediate step of from the end of an operation of adding a surface-crosslink-treating agent to a water-absorbent resin powder till the beginning of an operation of carrying out heating in the case where the production line of the water-absorbent resin includes a step of adding the surface-crosslink-treating agent to the water-absorbent resin powder and a step of heating the resultant mixture to thereby carry out surface-crosslinking treatment, wherein the surface-crosslink-treating agent includes a surface-crosslinking agent and water as essential components and wherein the hydrophilic organic solvent content of the surface-crosslink-treating agent has been reduced. Then, the present inventors have found out that the time needed for this intermediate step has a great influence on the absorption properties of the produced water-absorbent resin. And then the present inventors have found out that the above problems can be solved by setting the above time at a short time of within 5 minutes which cannot even be surmised from working modes having hitherto been known in public.

In production plants of the water-absorbent resin, generally, such as various reactors and treatment apparatuses are linked together by intermediate steps of carrying out conveyance and, if necessary, storage (e.g. refer to the aforementioned patent documents 1 to 3). As the plant scale becomes larger, the time which is spent on the intermediate steps increases unavoidably, too. Then, in cases of conventional production plants having common production scales (such that the production is in the range of tens of thousands of tons to hundreds of thousands of tons per year), it has been usual that the intermediate steps are designed on such a scale that the stagnation time therein can be in the range of tens of minutes to several hours.

The present invention has not been completed until it is found out to be important for producing the water-absorbent resin excellent in the absorption properties by using the surface-crosslink-treating agent (which includes the surface-crosslinking agent and water as essential components and of which the hydrophilic organic solvent content has been reduced) that the time, which is spent on the intermediate step of from the end of the operation of adding the surface-crosslink-treating agent to the water-absorbent resin powder till the beginning of the operation of carrying out heating, is set at an extremely short time.

According to the present inventors' findings, as to water-absorbent resins used in absorbent articles such as diapers, it is needless to say that, as has hitherto been known, it is necessary to see to particle diameter elements (i.e. mass-average particle diameter and ratio of powder having particle diameters of smaller than 150 µm) of the water-absorbent resins. However, in addition thereto, it is also important to see to two utterly new parameters, namely, the total absorption capacity and the absorption efficiency under load. Such a production process as mentioned above can easily produce a water-absorbent resin further satisfying the above two parameters while satisfying the design standards as set with attention directed to the particle diameter elements.

That is to say, a process according to the present invention for production of a water-absorbent resin comprises:

a step (1) of polymerizing a monomer component including an acid-group-containing unsaturated monomer as an essential component to thereby obtain a hydrogel polymer;

a step (2) of drying and pulverizing the resultant hydrogel polymer to thereby obtain a water-absorbent resin powder;

a step (3) of adding a surface-crosslink-treating agent to the resultant water-absorbent resin powder, wherein the surface-crosslink-treating agent includes a surface-crosslinking agent and water as essential components and has a hydrophilic organic solvent content of 0 to 10 mass % relative to the surface-crosslink-treating agent; and a step (4) of heating the resultant mixture to thereby carry out surface-crosslinking treatment;

wherein a time of from the end of the step (3) till the beginning of the step (4) is within 5 minutes.

In addition, a water-absorbent resin according to the present invention is a water-absorbent resin obtained by a process including the step of polymerizing and crosslinking a monomer component including acrylic acid and/or its salt (neutralized material) as a main component, with the water-absorbent resin being characterized by: having a mass-average particle diameter of 300 to 600 µm; including a powder having particle diameters of smaller than 150 µm in an amount of 0 to 10 mass % relative to the water-absorbent resin; and exhibiting a total absorption capacity of not less than 70 (g/g) and an absorption efficiency of not less than 70% under load, wherein the total absorption capacity and the absorption efficiency under load are defined by the following equations based on values given by absorption of a 0.90 mass % aqueous sodium chloride solution (25° C.) for 1 hour:

total absorption capacity(g/g)=absorption capacity(g/g)without load+monolayer absorption capacity(g/g)under load; and absorption efficiency(%)under load=monolayer absorption capacity(g/g)under load×100/absorption capacity(g/g)without load.

Furthermore, an absorbent article according to the present invention is an absorbent article for absorption of excreta and blood, which comprises the above water-absorbent resin according to the present invention.

Effects of the Invention

The present invention can provide: not only a water-absorbent resin which exhibits excellent balances between water absorption performances; but also a process by which the water-absorbent resin having excellent absorption properties can be produced even if no hydrophilic organic solvent is used, or even if its amount is extremely reduced, when carrying out the surface-crosslinking treatment in the process of producing the water-absorbent resin. The present invention can further provide a water-absorbent resin optimum to absorbent articles such as diapers.

DETAILED DESCRIPTION OF THE INVENTION

Hereinafter, detailed descriptions are given about the present invention. However, the scope of the present invention is not bound to these descriptions. And other than the following illustrations can also be carried out in the form of appropriate modifications of the following illustrations within the scope not departing from the spirit of the present invention.

The process according to the present invention for production of a water-absorbent resin comprises:

a step (1) of polymerizing a monomer component including an acid-group-containing unsaturated monomer as an essential component to thereby obtain a hydrogel polymer;

a step (2) of drying and pulverizing the resultant hydrogel polymer to thereby obtain a water-absorbent resin powder;

a step (3) of adding a surface-crosslink-treating agent to the resultant water-absorbent resin powder, wherein the surface-crosslink-treating agent includes a surface-crosslinking agent and water as essential components and has a hydrophilic organic solvent content of 0 to 10 mass % relative to the surface-crosslink-treating agent; and a step (4) of heating the resultant mixture to thereby carry out surface-crosslinking treatment.

The water-absorbent resin in the present invention refers to a water-swellable and water-insoluble crosslinked polymer which is formable into a hydrogel. The term "water-swellable" means being able to absorb water in a large amount of essentially not smaller than 5 times, favorably in the range of 50 to 1,000 times, of the own weight in ion-exchanged water. The term "water-insoluble" means that the uncrosslinked water-extractable component content (water-soluble polymer content) (specified in U.S. Pat. No. 6,187,872) of the water-absorbent resin is favorably in the range of 0 to 50 mass %, more favorably 0 to 25 mass %, still more favorably 0 to 20 mass %, particularly favorably 0 to 15 mass %, most favorably 0 to 10 mass %, relative to the water-absorbent resin.

Examples of the water-swellable and water-insoluble crosslinked polymer, which constitutes the water-absorbent resin in the present invention, include one or two or more of such as: partially-neutralized polymers of poly(acrylic acids); hydrolyzed graft polymers of starch-acrylonitrile; graft polymers of starch-acrylic acid; saponified copolymers of vinyl acetate-acrylic acid ester; hydrolyzed copolymers of acrylonitrile or acrylamide, or crosslinked polymers of these hydrolyzed copolymers; modified polymers of carboxyl-group-containing crosslinked polyvinyl alcohols; and crosslinked copolymers of isobutylene-maleic anhydride. However, there are preferred the partially-neutralized polymers of poly(acrylic acids) which are obtained by a process including the step of polymerizing and crosslinking a monomer component including acrylic acid and/or its salt (neutralized material) as a main component.

In the process according to the present invention for production of a water-absorbent resin, the hydrogel polymer has an acid group and/or its salt and is favorably obtained by a process including the step of polymerizing a monomer component including an acid-group-containing unsaturated monomer as an essential component. Incidentally, the acid-group-containing unsaturated monomer encompasses, also, a monomer which will contain the acid group by being hydrolyzed after the polymerization (e.g. acrylonitrile). However, there is preferred an acid-group-containing unsaturated monomer which has already contained the acid group during the polymerization.

In the present invention, it is favorable that the monomer component includes acrylic acid and/or its salt as a main component.

In the case where the monomer component includes acrylic acid and/or its salt as a main component, another monomer may be used jointly therewith. This jointly usable monomer is free of especial limitation if even its joint use permits the exercise of the effects of the present invention. However, examples thereof include water-soluble or hydrophobic unsaturated monomers such as: methacrylic acid, (anhydrous) maleic acid, fumaric acid, crotonic acid, itaconic acid, vinylsulfonic acid, 2-(meth)acrylamido-2-methylpropane-sulfonic acid, (meth)acryloxyalkanesulfonic acids, and their alkaline metal salts and ammonium salts; and N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethylene glycol (meth)acrylate, polyethylene glycol (meth)acrylate, isobutylene, and lauryl(meth)acrylate.

In the present invention, when the monomers other than the acrylic acid and/or its salt are used, the ratio of these monomers other than the acrylic acid and/or its salt is favorably in the range of 0 to 30 mol %, more favorably 0 to 10 mol %, relative to the total of the acrylic acid and/or its salt used as the main component. If the above monomers other than the acrylic acid and/or its salt are used in such a ratio, then the effects of the present invention are sufficiently exercised, so that the absorption performances of the resultant water-absorbent resin are still more enhanced, and further that the water-absorbent resin can be obtained at still lower costs.

In the process according to the present invention for production of a water-absorbent resin, the hydrogel polymer has a crosslinked structure. This crosslinked structure may be a self-crosslinked-type one obtained without any crosslinking agent, but is preferably a crosslinked structure obtained by copolymerization or reaction with a crosslinking agent (internal-crosslinking agent for water-absorbent resins) having at least two polymerizable unsaturated groups and/or at least two reactive groups per molecule.

Specific examples of the internal-crosslinking agents include N,N'-methylenebis(meth)acrylamide, (poly)ethylene glycol di(meth)acrylate, (poly)propylene glycol di(meth)acrylate, trimethylolpropane tri(meth)acrylate, glycerol tri(meth)acrylate, glycerol acrylate methacrylate, ethylene-oxide-modified trimethylolpropane tri(meth)acrylate, pentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, ethylene carbonate, propylene carbonate, polyethylenimine, and glycidyl(meth)acrylate.

The internal-crosslinking agents may be used either alone respectively or in appropriate combinations with each other. In addition, the internal-crosslinking agents may be added to the reaction system either in a lump or divisionally. In the case where the internal-crosslinking agents are used, it is favorable, for sufficiently exercising the effects of the present invention, that a compound having at least two polymerizable unsaturated groups is used during the polymerization.

The amount of these internal-crosslinking agents as used is favorably in the range of 0.001 to 2 mol %, more favorably 0.005 to 0.5 mol %, still more favorably 0.01 to 0.2 mol %, particularly favorably 0.03 to 0.15 mol %, relative to the aforementioned monomer component (exclusive of the crosslinking agents). In the case where the amount of the above internal-crosslinking agent as used is smaller than 0.001 mol % or larger than 2 mol %, there are disadvantages in that there is a possibility that the effects of the present invention cannot sufficiently be exercised, so there is a possibility that the resultant water-absorbent resin cannot exercise sufficient absorption properties.

In the case where the internal-crosslinking agent is used to introduce the crosslinked structure into the inside of the polymer, it is enough that the internal-crosslinking agent is added to the reaction system before, on the way of, or after the polymerization of the monomer component, or after its neutralization.

There is no especial limitation on the method for polymerizing the monomer component in order to obtain the hydrogel polymer in the process according to the present invention for production of a water-absorbent resin. Examples thereof include aqueous solution polymerization, reversed-phase suspension polymerization, bulk polymerization, and precipitation polymerization. However, from such as viewpoints of the performance, the facility of polymerization control, and the absorption properties of a swollen gel, it is favorable to carry out the aqueous solution polymerization or reversed-phase suspension polymerization in which the monomer component is used in the form of an aqueous solution.

In the case where the monomer component is used in the form of an aqueous solution, the concentration of the monomer component in this aqueous solution (which may hereinafter be referred to as aqueous monomer solution). depends on the temperature of the aqueous solution or the kind of the monomer component and is therefore not especially limited. However, this concentration is favorably in the range of 10 to 70 mass %, more favorably 20 to 60 mass %, relative to the aqueous monomer solution. In addition, when the above aqueous solution polymerization is carried out, a solvent other than water may be used jointly therewith if necessary. The kind of this solvent which is jointly used is not especially limited.

The reversed-phase suspension polymerization is a polymerization method in which the aqueous monomer solution is suspended in a hydrophobic organic solvent, and such a polymerization method is, for example, disclosed in US patents such as U.S. Pat. No. 4,093,776, U.S. Pat. No. 4,367,323, U.S. Pat. No. 4,446,261, U.S. Pat. No. 4,683,274, and U.S. Pat. No. 5,244,735. The aqueous solution polymerization is a polymerization method in which the aqueous monomer solution is polymerized without any dispersing solvent, and such a polymerization method is, for example, disclosed in: US patents such as U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, and U.S. Pat. No. 5,380,808; and European patents such as EP 0811636, EP 0955086, and EP 0922717. It is also possible that such as monomer components and initiators exemplified for these polymerization methods are applied to the present invention.

When the above polymerization is initiated, there can be used, for example, the following: radical polymerization initiators such as potassium persulfate, ammonium persulfate, sodium persulfate, t-butyl hydroperoxide, hydrogen peroxide, and 2,2'-azobis(2-amidinopropane)dihydrochloride; and photoinitiators such as 2-hydroxy-2-methyl-1-phenyl-propan-1-one. From the viewpoint of such as properties of the resultant water-absorbent resin, the amount of the polymerization initiator as used is favorably in the range of 0.001 to 2 mol % (relative to the entire monomer component), more favorably 0.01 to 0.1 mol % (relative to the entire monomer component).

The hydrogel polymer is obtained from the step of polymerizing the monomer component including the acid-group-containing unsaturated monomer as an essential component in the above way.

After having been divided into small pieces if necessary, the hydrogel polymer obtained by the above polymerization is dried and pulverized. The pulverization may be carried out before, at the same time as, or after the drying. Favorably, the hydrogel polymer is pulverized after the drying.

In the present invention, favorably, the drying is carried out to the hydrogel polymer which is particulate (for example, its mass-average particle diameter is not larger than 2 cm, favorably not larger than 1 cm, more favorably not larger than 5 mm). As to methods for dividing the hydrogel polymer into small pieces in order to particulate it in the present invention, such as kneaders may be used to carry out the dividing into small pieces at the same time as the polymerization, or the dividing into small pieces may be carried out separately after the polymerization. The dividing into small pieces at the same time as the polymerization and the dividing into small pieces after the polymerization may be jointly used. Incidentally, in the case where the hydrogel polymer is not dried in the particulate form, for example, in the case where the hydrogel polymer is dried in such as a filmy form, there is a possibility that the resultant properties may be inferior and that the resultant particle size may deviate from the favorable ranges.

As to the particle diameters of the hydrogel polymer before the drying, its mass-average particle diameter is favorably in the range of 45 to 4,000 μm, more favorably 50 to 2,000 μm, still more favorably 100 to 1,500 μm, particularly favorably 200 to 1,000 μm, from the viewpoint of the drying efficiency and the properties. Incidentally, in the case where the mass-average particle diameter of the hydrogel polymer deviates from the above range, there is a possibility of causing such as deterioration of the water absorption capacity and increase of the water-extractable component content as to the resultant water-absorbent resin.

Examples of devices suitable for the dividing into small pieces include: kneaders; lengthwise cutting type slitters with cutter blades; crosswise cutting type slitters with cutter blades; cutter type pulverizers with rotary blades; and meat choppers of predetermined opening diameters.

In the process according to the present invention for production of a water-absorbent resin, the hydrogel polymer gets dried indispensably. Incidentally, the drying in the present invention refers to bringing the above hydrogel polymer into a solid state where its solid content (defined by the drying loss at 180° C. in 3 hours) is not lower than 80 mass %, favorably not lower than 85 mass %, more favorably not lower than 90 mass %, particularly favorably not lower than 93 mass %, relative to the dried polymer. Incidentally, the drying in the present invention does not necessarily need to give a dried polymer having a solid content of 100 mass % (water content of zero).

The drying method usable in the present invention is not especially limited. For example, there can be used at least one of drying methods such as: hot-air drying; thin-film drying with such as drum driers; reduced-pressure drying methods; agitation drying; and fluidized-bed drying. It does not especially matter whether the drying is carried out continuously or batchwise. From the viewpoint of the properties and the drying efficiency, the hot-air drying (particularly, continuous hot-air drying) is favorably used in the present invention. For example, static drying on a belt will do for it.

From the viewpoint of the drying efficiency, the above hot-air drying will do, for example, if it is carried out in the following way: the particulate hydrogel polymer is layered on a metal gauze or a punched metal with perforations or slits, and then hot air is passed through spaces between the layered particles in vertical or horizontal directions, preferably in vertical directions, to the gel. As to the metal gauze or perforation diameter, for example, in the case of the perforations or metal gauze, it will do if it has air-through openings of favorably about 0.1 to about 5 mm, more favorably about 0.2 to about 2 mm. In addition, as to the layering of the gel on the metal gauze or punched metal, it will do from the viewpoint of the after-drying properties if the particulate hydrogel polymer is layered in a definite thickness of favorably 1 to 20 cm, more favorably 1.5 to 10 cm, still more favorably 2 to 8 cm.

When the above hydrogel polymer is dried, the drying temperature will do from the viewpoint of the properties and the productivity if it is set usually favorably at not lower than 100° C., more favorably in the range of 110 to 230° C., still more favorably 130 to 200° C., particularly favorably 150 to 190° C. Incidentally, the drying temperature is defined as temperature of the material or temperature of a heat medium (e.g. hot air), but is favorably defined as the temperature of the heat medium. In addition, the drying temperature during the drying period may be constant or may appropriately be varied in the above temperature range on the way of the drying.

Furthermore, when the hot-air drying is carried out, the dew point of the hot air is favorably in the range of 40 to 100° C., more favorably 50 to 90° C., still more favorably 60 to 85° C., from the viewpoint of the properties and the energy efficiency.

Incidentally, it is also mentioned herein that, after having been dried in the layered state, the particulate hydrogel polymer tends to be a blocky dried material which has lost the flowability as a result of agglomeration between particles due to the drying. Such a blocky dried material is an agglomerate of dried polymer particles, but has continuous spaces and gas permeability into blocks. However, this blocky dried material lacks the flowability due to the agglomeration and therefore needs to be pulverized (disintegrated).

In the present invention, the hydrogel polymer is dried in the above way and further is pulverized as well. The pulverization may be carried out before, at the same time as, or after the drying. However, the hydrogel polymer is favorably pulverized after the drying and more favorably further classified after having been pulverized.

In the present invention, the drying and the pulverization, and further the classification if necessary, are favorably carried out in a mode of a series of steps, and the time of from an outlet of the drier to an inlet of the pulverizer is favorably within 10 minutes, more favorably within 5 minutes, still more favorably within 2 minutes.

In the present invention, the method for the pulverization is free of especial limitation if it can form the dried polymer or its agglomerate (blocky material) into a flowable powder, favorably a powder having a mass-average particle diameter of not larger than 2 mm. For example, there can be used at least one of: methods in which the pulverization is carried out with such as hammer type pulverizers, roll type pulverizers, and jet stream type pulverizers; and hitherto publicly known various pulverization or disintegration methods. In addition, in the case where the agglomeration during the drying is weak, the dried polymer may be given vibration and thereby classified to loosen the agglomeration of the polymer, thus carrying out the pulverization even if no pulverizer is especially used.

In the present invention, after the above pulverization, further the classification is, if necessary, favorably carried out, so that coarse particles and a fine powder are removed. The mass-average particle diameter of the water-absorbent resin powder, as obtained in the above way, is determined appropriately for the object. However, in order to sufficiently exercise the effects of the present invention, the water-absorbent resin powder has a mass-average particle diameter in the range of favorably 300 to 600 µm, more favorably 300 to 550 µm, particularly favorably 380 to 550 µm. In addition, the water-absorbent resin powder being finally obtained includes a powder having particle diameters of smaller than 150 µm in an amount of favorably 0 to 10 mass %, more favorably 0 to 8 mass %, still more favorably 0 to 5 mass %, particularly favorably 0 to 3 mass %, relative to the water-absorbent resin powder. In addition, the water-absorbent resin powder being finally obtained includes particles having particle diameters of smaller than 150 µm and particles having particle diameters of not smaller than 850 µm in a total amount of favorably 0 to 15 mass %, more favorably 0 to 10 mass %, still more favorably 0 to 5 mass %, relative to the water-absorbent resin powder.

Particularly, in the present invention, it is favorable that the water-absorbent resin powder has a mass-average particle diameter of 300 to 600 µm and includes a powder having particle diameters of smaller than 150 µm in an amount of favorably 0 to 10 mass %, more favorably 0 to 5 mass %, most favorably 0 to 3 mass %, relative to the water-absorbent resin powder.

The bulk density of the water-absorbent resin powder diversely varies with the bulk density (g/cm$^3$) as unambiguously determined by the monomer composition. However, in the case where the water-absorbent resin is sodium polyacrylate, particularly, sodium polyacrylate having a neutralization degree of 50 to 90 mol %, more particularly, sodium polyacrylate having a neutralization degree of 60 to 80 mol %, then its bulk density is usually favorably not less than 0.63 g/ml, particularly favorably not less than 0.65 g/ml. Incidentally, the bulk density will do if it is measured with a device according to JIS K-3362. In the present invention, by the pulverization, the water-absorbent resin powder comes into a less scaly, more roundish, and uniform shape, and therefore its bulk density tends to become higher. Therefore, the bulk density is favorably adjusted so as to be in the range of 0.65 to 0.89 g/ml, more favorably 0.67 to 0.88 g/ml, still more favorably 0.73 to 0.87 g/ml, yet still more favorably 0.74 to 0.86 g/ml, yet still more favorably 0.75 to 0.85 g/ml, after the pulverization. In the case where the bulk density of the water-absorbent resin powder deviates from the above range after the pulverization, there is a possibility that the effects of the present invention may not sufficiently be exercised.

After the above pulverization, the coarse particles (e.g. 850 µm-on product) and the fine powder (e.g. 150 µm-pass product) will do if they are appropriately recycled as the case may be. They will do if: the coarse particles are re-pulverized and the fine particles are removed or recovered, thereby giving the aforementioned particle diameter distribution. However, in the present invention, because the particle diameter distribution is narrow, the necessity of the above recycling greatly reduces. Incidentally, methods for recycling the fine powder of the water-absorbent resin are disclosed in such as U.S. Pat. No. 4,950,692, U.S. Pat. No. 5,064,582, U.S. Pat. No. 5,264, 495, U.S. Pat. No. 5,478,879, EP 0812873, EP 0885917, and EP 0844270. It is also possible to apply these fine powder recycling methods to the present invention. In addition, the amount of the fine powder being recycled is favorably not larger than 30 mass %, more favorably not larger than 15 mass %, particularly favorably in the range of 1 to 10 mass %, most favorably 2 to 8 mass %, of the entirety. In the present invention, because the water-absorbent resin powder having the narrow particle diameter distribution is obtained with high productivity by the pulverization, there are advantages in that a water-absorbent resin powder having a still narrower particle diameter distribution is obtained by recycling a small amount of fine powder.

The water-absorbent resin powder, as obtained in the above way, exhibits an absorption capacity of favorably not less than 40 g/g, more favorably not less than 45 g/g, still more favorably not less than 50 g/g, particularly favorably not less than 55 g/g, for a 0.90 mass % aqueous sodium chloride solution (physiological saline solution) without load. As the absorption capacity of the above water-absorbent resin powder which is a base polymer becomes higher, there increases the favorability for obtaining the water-absorbent resin having excellent absorption properties.

In the process according to the present invention for production of a water-absorbent resin, there are included: the step (3) of adding a surface-crosslink-treating agent to the resultant water-absorbent resin powder, wherein the surface-crosslink-treating agent includes a surface-crosslinking agent and water as essential components and has a hydrophilic organic solvent content of 0 to 10 mass % relative to the surface-crosslink-treating agent; and the step (4) of heating the resultant mixture to thereby carry out surface-crosslinking treatment.

The surface-crosslinking agents for carrying out the surface-crosslinking treatment are various and not especially limited. However, from the viewpoint of such as enhancement of the properties of the resultant water-absorbent resin, there are preferred such as: polyhydric alcohol compounds; epoxy compounds; polyamine compounds or products from their condensation with haloepoxy compounds; oxazoline compounds; mono-, di-, or polyoxazolidinone compounds; cyclic urea compounds; polyvalent metal salts; and alkylene carbonate compounds.

The surface-crosslinking agent usable in the present invention is not especially limited. However, for example, it is possible to use surface-crosslinking agents which are exemplified in such as U.S. Pat. No. 6,228,930, U.S. Pat. No. 6,071,976, and U.S. Pat. No. 6,254,990. Examples thereof include: polyhydric alcohol compounds (e.g. mono-, di-, tri-, tetra-, or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol); epoxy compounds (e.g. ethylene glycol diglycidyl ether and glycidol); polyamine compounds (e.g. ethylenediamine, diethylenetriamine, triethylenetetramine, tetraethylenepentamine, pentaethylenehexamine, polyethylenimine, and polyamidepolyamine); haloepoxy compounds (e.g. epichlorohydrin, epibromohydrin, and α-methylepichlorohydrin); condensation products between the above polyamine compounds and the above haloepoxy compounds; oxazolidinone compounds (e.g. 2-oxazolidinone); cyclic urea compounds; and alkylene carbonate compounds (e.g. ethylene carbonate). These may be used either alone respectively or in combinations with each other. For sufficiently exercising the effects of the present invention, it is favorable to indispensably use the polyhydric alcohol compounds among these surface-crosslinking agents. As the polyhydric alcohol compounds, those which have 2 to 10 carbon atoms are favorable, and those which have 3 to 8 carbon atoms are more favorable.

The amount of the surface-crosslinking agent, being used, depends upon such as compounds being used and their combination, but is favorably in the range of 0.001 to 10 mass %, more favorably 0.01 to 5 mass %, relative to the water-absorbent resin powder.

The surface-crosslink-treating agent, which is used in the process according to the present invention for production of a water-absorbent resin, includes the aforementioned surface-crosslinking agent and water as essential components and has a hydrophilic organic solvent content of 0 to 10 mass % relative to the surface-crosslink-treating agent.

The amount of the water, which is contained in the surface-crosslink-treating agent in the present invention, depends upon water content of the water-absorbent resin powder being used, but is favorably in the range of 0.5 to 20 mass %, more favorably 0.5 to 10 mass %, particularly favorably 0.5 to 7 mass %, most favorably 0.5 to 4 mass %, relative to the water-absorbent resin powder.

The hydrophilic organic solvent content of the surface-crosslink-treating agent in the present invention is in the range of 0 to 10 mass % and favorably 0 to 8 mass %, more favorably 0 to 5 mass %, still more favorably 0 to 3 mass %, yet still more favorably 0 to 1 mass %, particularly favorably 0 mass % (a substantially not contained state), relative to the surface-crosslink-treating agent. By the process according to the present invention, the properties are enhanced, and the below-mentioned novel water-absorbent resin is obtained. Furthermore, as to this process, the use of the surface-crosslink-treating agent, of which the hydrophilic organic solvent content has been reduced, solves the problems of environmental contamination due to waste liquids and/or waste gases discharged during the production, and further, gratifies the use circumstances such that the water-absorbent resin is used for the sanitary materials which contact directly with human bodies.

Hereupon, the hydrophilic organic solvent will do if it is an organic compound (usually having no or only one functional group) which does not make a crosslinking reaction with the acid group, favorably the carboxyl group, possessed by the water-absorbent resin. Specific examples thereof include: alcohols (e.g. ethyl alcohol, propyl alcohol, isopropyl alcohol); ketones (e.g. acetone); ethers (e.g. dioxane, alkoxy (poly)ethylene glycols, tetrahydrofuran); amides (e.g. ε-caprolactam); and sulfoxides (e.g. dimethyl sulfoxide).

In the present invention, the hydrophilic organic solvent refers to an organic compound which can dissolve into liquid water at normal temperature. Usually, its solubility is usually not less than 1 g, favorably not less than 10 g, in 100 g of water of normal temperature. In the present invention, the hydrophilic organic solvent needs to be a liquid at normal temperature. However, the solvent which exercises at the maximum the effects intended in the present invention is a volatile hydrophilic organic solvent, for example, a hydrophilic organic solvent having a boiling point of favorably 50 to 170° C., more favorably 60 to 150° C., particularly favorably 60 to 130° C.

Incidentally, in the case where the crosslinking agent is an organic compound, the distinction between the crosslinking agent and the hydrophilic organic solvent is as follows. Usually, a compound which substantially does not make a crosslinking reaction with the water-absorbent resin (compound which substantially does not change the properties of the water-absorbent resin) under certain selected reaction conditions is classified as the hydrophilic organic solvent. On the other hand, for example, in the case where a crosslinking reaction runs by mixing the water-absorbent resin with an organic compound or its aqueous solution and then heating them, this organic compound is defined as the crosslinking agent.

The surface-crosslink-treating agent in the present invention may further include components other than the above-mentioned, in the range not spoiling the effects of the present invention. Examples of such components include water-insoluble fine particle powders and surfactants.

In the process according to the present invention for production of a water-absorbent resin, the method for adding the surface-crosslink-treating agent to the water-absorbent resin powder is not especially limited. However, examples thereof include: a method in which the surface-crosslink-treating agent is dropwise added to the water-absorbent resin powder to mix them together; and a method in which the surface-crosslink-treating agent is sprayed to the water-absorbent resin powder.

When the surface-crosslink-treating agent is added to the water-absorbent resin powder, it is favorable to use a mixing apparatus in order to effectively carry out the addition. Although not especially limited, the usable mixing apparatus has great mixing power favorably for uniformly and surely mixing the water-absorbent resin powder and the surface-crosslink-treating agent together. Examples of the mixing apparatus include cylinder type mixers, double-wall cone type mixers, V-character-shaped mixers, ribbon type mixers, screw type mixers, fluidized-furnace rotary disk type mixers, gas current type mixers, twin-arm kneaders, internal mixers, pulverizing type kneaders, rotary mixers, and screw type extruders. It does not matter whether the mixing speed is high or not.

In the process according to the present invention for production of a water-absorbent resin, the water-absorbent resin powder favorably has a temperature in the range of 40 to 80° C., more favorably 45 to 80° C., still more favorably 50 to 70° C., when the surface-crosslink-treating agent is added thereto. In the case where the water-absorbent resin powder has a temperature of lower than 40° C. when the surface-crosslink-treating agent is added thereto, there are disadvantages in that, when the water-absorbent resin is produced under high-humidity environments, dew condensation tends to occur to thus cause troubles. In the case where the water-absorbent resin powder has a temperature of higher than 80° C. when the surface-crosslink-treating agent is added thereto, there are disadvantages in that it tends to be impossible to uniformly carry out the surface-crosslinking treatment.

In the process according to the present invention for production of a water-absorbent resin, although not especially limited, the temperature of the surface-crosslink-treating agent when adding the surface-crosslink-treating agent to the water-absorbent resin powder is, favorably for sufficiently exercising the effects of the present invention, a temperature which substantially does not exceed that of the water-absorbent resin powder which undergoes the addition of the surface-crosslink-treating agent.

In the process according to the present invention for production of a water-absorbent resin, the surface-crosslinking treatment is carried out by heating after the surface-crosslink-treating agent has been added to the water-absorbent resin powder.

The heating temperature (temperature of the material or temperature of the heat medium) is favorably in the range of 60 to 260° C., more favorably 80 to 240° C., still more favorably 100 to 220° C., particularly favorably 120 to 200° C. The heating duration is favorably in the range of 1 to 120 minutes, more favorably 10 to 100 minutes, still more favorably 20 to 90 minutes, particularly favorably 30 to 60 minutes. Favorable examples of combinations of the heating temperature and the heating duration include the following: at 180° C. for 1 to 90 minutes and at 200° C. for 1 to 60 minutes.

In the process according to the present invention for production of a water-absorbent resin, it is important that the heating is begun beyond 0 second and within 5 minutes from the end of the addition of the surface-crosslink-treating agent to the water-absorbent resin powder. Specifically, it is important that the time of from the end of the aforementioned step (3) till the beginning of the aforementioned step (4) is beyond 0 second and within 5 minutes. This time is favorably within 4 minutes, more favorably within 3 minutes, still more favorably within 2 minutes, particularly favorably within 1 minute. The effects of the present invention are exercised by, in this way, beginning the heating within 5 minutes from the end of the addition of the surface-crosslinking-treating agent to the water-absorbent resin powder. In the case where the time of from the end of the addition of the surface-crosslink-treating agent to the water-absorbent resin powder till the beginning of the heating is beyond 5 minutes, the effects of the present invention cannot be exercised.

Incidentally, in the present invention, the time of from the end of the addition of the surface-crosslink-treating agent to the water-absorbent resin powder till the beginning of the heating refers specifically to the time of from the end of the step (3) (of adding the surface-crosslink-treating agent to the water-absorbent resin powder) till the beginning of the step (4) (of heating the resultant mixture to thereby carry out the surface-crosslinking treatment), for example, till the charging into an apparatus for the step (4). In addition, in the case of the continuous production, the above time can easily be calculated from such as: the amount of the water-absorbent resin being fed (supplied) per unit time; the stagnation time of the water-absorbent resin in an apparatus for adding the surface-crosslink-treating agent thereto to mix them together; and the transportation time of till charging the resultant mixture into the apparatus for the step (4) of heating it to thereby carry out the surface-crosslinking treatment. Specifically, the above time may be determined by actually measuring or calculating the powder migration time of from an outlet of the mixer to an inlet of the heater.

As a method for surface-crosslinking the water-absorbent resin, working examples as set out in JP-A-508517/1996 (Kohyo) disclose such as arts including the steps of: continuously mixing the water-absorbent resin powder (being fed at 1,000 kg/h) with a treating agent (surface-crosslinking agent); and then once storing the resultant mixture; and then continuously heating the mixture. Like this, in conventional arts, generally, once intermediately storing the water-absorbent resin has been carried out as a cushion linking the steps together between the mixer for the surface-crosslinking agent and the subsequent reactor (heater).

In addition, in the case where the water-absorbent resin is continuously produced, the steps are linked together by use of transporters. However, as the production scale of the water-absorbent resin increases into the range of tens of thousands of tons to hundreds of thousands of tons per year, not less than a definite conveyance distance (conveyance time) between the steps has become necessary besides the above storage. Therefore, it has been the actual situation that there are intermediate steps (for the conveyance or storage) of around ten to tens of minutes, as the case may be, several hours, between the steps.

However, in order to use the specific surface-crosslink-treating agent which includes the surface-crosslinking agent and water as essential components and of which the hydrophilic organic solvent content has been reduced, the present inventors have directed their attention to the intermediate step between the mixer for the surface-crosslink-treating agent and the subsequent reactor (heater) and then found out that the omission or simplification of such an intermediate step is important for enhancing the properties of the water-absorbent resin. This omission or simplification of the intermediate step enables not only the enhancement of the performances of the water-absorbent resin but also the reduction of the investment in plant and equipment.

Examples of production facilities means for achieving the present invention include a facilities layout such that the reactor (heater) is set below the apparatus for adding and mixing the surface-crosslink-treating agent. Specifically, the water-absorbent resin with which the surface-crosslink-treating agent has been mixed is discharged from the apparatus for carrying out the step (3) (of adding the surface-crosslink-treating agent to the water-absorbent resin powder), and then freely falls, and then is charged into the surface treatment reactor (heater). Thereby the time of from the end of the step (3) till the beginning of the step (4) is shortened.

The above process according to the present invention for production of a water-absorbent resin provides the below-mentioned novel water-absorbent resin.

Specifically, this process provides the water-absorbent resin according to the present invention which is a water-absorbent resin obtained by a process including the step of polymerizing and crosslinking a monomer component including acrylic acid and/or its salt (neutralized material) as a main component, with the water-absorbent resin being characterized by: having a mass-average particle diameter of 300 to 600 μm; including a powder having particle diameters of smaller than 150 μm in an amount of 0 to 10 mass % relative to the water-absorbent resin; and exhibiting a total absorption capacity of not less than 70 (g/g) and an absorption efficiency of not less than 70% under load.

The fact that the above water-absorbent resin according to the present invention is novel has been confirmed not only by analyzing the current state of a large number of commercially available products (e.g. water-absorbent resins, diapers) in the worldwide range, but also by comparatively evaluating many arts which have hitherto been proposed.

The two novel parameters found out by the present inventors, namely, the total absorption capacity and the absorption efficiency under load, are defined by the below-mentioned equations based on values given by absorption of a 0.90 mass % aqueous sodium chloride solution (25° C.) for 1 hour. Detailed descriptions about the measurement of these values for 1 hour are given in the below-mentioned detailed description of the preferred embodiments. Hereupon, the aforementioned equations are as follows:

total absorption capacity(g/g)=absorption capacity(g/g)without load+monolayer absorption capacity(g/g)under load; and absorption efficiency(%)under load=monolayer absorption capacity(g/g)under load×100/absorption capacity(g/g)without load.

The novel water-absorbent resin according to the present invention is a water-absorbent resin which has the aforementioned particle diameters and exhibits the total absorption capacity and the absorption efficiency under load in the aforementioned ranges. However, it is favorable that this resin is a surface-crosslinked one and further has the below-mentioned particle diameter elements (mass-average particle diameter, ratio of powder having particle diameters of smaller than 150 μm, particle diameter distribution) and exhibits the absorption capacity without load, the monolayer absorption capacity under load, the total absorption capacity, and the absorption efficiency under load in the below-mentioned ranges. The novel water-absorbent resin according to the present invention is favorably used jointly with additives (e.g. deodorants, inorganic powders).

The water-absorbent resin according to the present invention is free of limitation in respect to its production process if it is controlled in respect to the particle diameter elements (mass-average particle diameter, ratio of powder having particle diameters of smaller than 150 μm), the total absorption capacity, and the absorption efficiency under load. However, this resin can easily be obtained by a process including the steps of: polymerizing and crosslinking a monomer component including acrylic acid and/or its salt (neutralized material) as a main component; and then controlling the particle diameters of the resultant water-absorbent resin in the aforementioned range; and then surface-crosslinking the water-absorbent resin, when particularly processing the water-absorbent resin by the novel surface-crosslinking treatment aforementioned about the production process according to the present invention.

Hereinafter, further descriptions are given about the water-absorbent resin obtained by the production process according to the present invention or the novel water-absorbent resin according to the present invention.

The water-absorbent resin, as obtained by carrying out the surface-crosslinking treatment in the aforementioned way, is adjusted (regulated) to a specific particle size favorably for sufficiently exercising the effects of the present invention.

This particle size is favorably such that: particles of smaller than 850 μm but not smaller than 150 μm comprise not less than 90 mass % of the entirety, and particles of not smaller than 300 μm comprise not less than 60 mass % of the entirety; and more favorably such that: the particles of smaller than 850 μm but not smaller than 150 μm comprise not less than 95 mass %, still more favorably not less than 98 mass %, of the entirety. In addition, the particles of not smaller than 300 μm comprise more favorably not less than 65 mass %, still more favorably not less than 70 mass %, particularly favorably not less than 75 mass %, of the entirety.

The mass-average particle diameter of the water-absorbent resin in the present invention is favorably in the range of 200 to 700 μm, more favorably 300 to 600 μm, particularly favorably 380 to 550 μm, most favorably 400 to 500 μm. The mass-average particle diameter of the water-absorbent resin may be adjusted (regulated) by such as agglomeration, if necessary.

The water-absorbent resin in the present invention includes a powder having particle diameters of smaller than 150 μm in an amount of favorably 0 to 10 mass more favorably 0 to 8 mass %, still more favorably 0 to 5 mass %, particularly favorably 0 to 3 mass %, relative to the water-absorbent resin.

In addition, as to the water-absorbent resin in the present invention, the logarithmic standard deviation (σζ; the decrease of its value indicates that the particle diameter distribution becomes narrower) (which is determined in the below-mentioned way) of the particle diameter distribution is favorably in the range of 0.25 to 0.50, more favorably 0.27 to 0.48, still more favorably 0.30 to 0.45.

Logarithmic standard deviation of particle diameter distribution: This is a value obtained by a process including the steps of: classifying the water-absorbent resin with JIS standard sieves having mesh opening sizes of 850 μm, 710 μm, 600 μm, 500 μm, 425 μm, 300 μm, 212 μm, 150 μm, and 45 μm; and then plotting the percentages R of the residues (remaining on these sieves) on a logarithmic probability paper; and then, from its result, determining a particle diameter $X_1$ when R=84.1 mass % and a particle diameter $X_2$ when R=15.9 mass %; and then introducing these determined values into the following equation.

$$\sigma\zeta = 0.5 \times \ln(X_2/X_1)$$

For σζ to be more than 0.50 indicates such a broad particle diameter distribution of a powder as to cause such as segregation and powder-supply amount errors in the handling of the powder. Therefore, such σζ is not very favorable to practical use for such as diapers. On the other hand, for σζ to be less than 0.25 indicates such a narrow particle diameter distribution of a powder as to: be favorable for the handling of the powder; but involve the increase of the amounts of the coarse particles and fine powder being recycled for the adjustment (regulation) of the particle size; and thus cause the decrease of the production amount per unit time. Therefore, such σζ is not very favorable.

The water-absorbent resin in the present invention exhibits an absorption capacity of favorably not less than 33 g/g, more favorably not less than 35 g/g, still more favorably not less than 38 g/g, particularly favorably not less than 40 g/g, most favorably not less than 45 g/g, for a 0.90 mass % aqueous sodium chloride solution (physiological saline solution) without load. In the case where the absorption capacity for the 0.90 mass % aqueous sodium chloride solution (physiological saline solution) without load is less than 33 g/g, there is a possibility that the effects of the present invention cannot sufficiently be exercised. For example, the case of the use for diapers results in a small absorption amount and much leakage during practical use. Incidentally, to increase the absorption capacity without load to more than 80 g/g involves decreasing the amounts of the internal-crosslinking agent and surface-crosslinking agent being used, and thus has a possibility of hindering the effects of the present invention from being exercised sufficiently, and is therefore not very favorable.

The water-absorbent resin in the present invention exhibits a monolayer absorption capacity of favorably not less than 25 g/g, more favorably not less than 30 g/g, still more favorably not less than 35 g/g, for the 0.90 mass % aqueous sodium chloride solution (physiological saline solution) under a load of 1.9 kPa. In the case where the monolayer absorption capacity for the 0.90 mass % aqueous sodium chloride solution (physiological saline solution) under the load of 1.9 kPa is less than 25 g/g, there is a possibility that the effects of the present invention cannot sufficiently be exercised. For example, an eruption of the skin (buttocks) is caused by liquids on surfaces of diapers during practical use. Incidentally, the monolayer absorption capacity under load has no especial upper limit. The high it is, the more favorable it is. However, to increase this absorption capacity to not less than a definite value has a possibility of causing such as extreme deterioration of the productivity and, also in property aspects, increase of the water-extractable component content and the gel strength. Therefore, from the viewpoint of the cost performance (production cost per absorption capacity) and the balance between properties, the upper limit may be about 60 g/g.

The water-absorbent resin in the present invention exhibits a total absorption capacity of favorably not less than 70 g/g, more favorably not less than 74 g/g, still more favorably not less than 78 g/g, particularly favorably not less than 82 g/g. The total absorption capacity is the sum of the absorption capacity for the 0.90 mass % aqueous sodium chloride solution (physiological saline solution) without load and the monolayer absorption capacity for the 0.90 mass % aqueous sodium chloride solution (physiological saline solution) under the load of 1.9 kPa, and indicates the total absorption capacity in a state without load and in a state under load. In the case where the total absorption capacity is less than 70 g/g, there is a possibility that the effects of the present invention cannot sufficiently be exercised. For example, the case of the use for diapers results in a small absorption amount and much leakage during practical use, or an eruption of the skin (buttocks) is caused by liquids on surfaces of diapers during practical use. Incidentally, to increase the total absorption capacity to more than 140 g/g involves carrying out the steps of such as polymerization, drying, pulverization, particle size adjustment (regulation), and surface-crosslinking with the productivity much dropped, and is therefore not very favorable in point of costs.

The water-absorbent resin in the present invention exhibits an absorption efficiency of favorably not less than 70%, more favorably not less than 74%, still more favorably not less than 78%, particularly favorably not less than 82%, under load. The absorption efficiency under load is the ratio in percentage of the monolayer absorption capacity for the 0.90 mass % aqueous sodium chloride solution (physiological saline solution) under the load of 1.9 kPa to the absorption capacity for the 0.90 mass % aqueous sodium chloride solution (physiological saline solution) without load, and indicates an absorption property under load. If the absorption efficiency under load is high, then the absorption capacity little varies with the pressure. In the case where the absorption efficiency under load is less than 70%, there is a possibility that the effects of the present invention cannot sufficiently be exercised. For example, the case of the use for diapers results in a small absorption amount and much leakage during practical use, or an eruption of the skin (buttocks) is caused by liquids on surfaces of diapers during practical use. Incidentally, to increase the absorption efficiency under load to more than 150% involves carrying out the steps of such as polymerization, drying, pulverization, particle size adjustment (regulation), and surface-crosslinking with the productivity much dropped, and is therefore not very favorable in point of costs.

The water-absorbent resin in the present invention particularly favorably exhibits the total absorption capacity of not less than 70 g/g and the absorption efficiency of not less than 70% under load.

The water content and water-extractable component content of the water-absorbent resin according to the present invention are in the aforementioned ranges, and the residual monomer content of this resin is usually in the range of 0 to 1,000 mass ppm, favorably 0 to 500 mass ppm, more favorably 0 to 400 mass ppm.

If necessary, the water-absorbent resin in the present invention may be provided with various functions by further adding thereto additives such as: deodorants; antibacterial agents; perfumes; various inorganic powders; foaming agents; pigments; dyes; hydrophilic short fibers; plasticizers; pressure-sensitive adhesives; surfactants; manure; oxidants; reducing agents; chelating agents; antioxidants; water; water-soluble polymers; binders; and salts.

Incidentally, as to the present invention, in the case where the additive is substantially united with the water-absorbent resin by adding the additive to the water-absorbent resin to combine them together (due to such as absorption, adsorption, or mixing), the resultant material is a mixture in a sense. However, as long as this mixture of the water-absorbent resin and the additive (this mixture is commonly called "water-absorbing agent") satisfies the aforementioned ranges of the particle diameters, the total absorption capacity, and the absorption efficiency under load, this mixture of the water-absorbent resin and the additive is also taken as the water-absorbent resin which is referred to in the present invention. In other words, in the present invention, the water-absorbent resin, which is obtained by a process including the step of polymerizing and crosslinking a monomer component including acrylic acid and/or its salt (neutralized material) as a main component, is a conception encompassing what is commonly called "water-absorbing agent" obtained by combining the water-absorbent resin with the above additive. Then, the content of the water-absorbent resin in such a water-absorbing agent is favorably in the range of 70 to 100 mass %, more favorably 80 to 100 mass %, particularly favorably 90 to 100 mass %, relative to the water-absorbing agent. The water-absorbing agent may contain water as a trace component.

Favorable examples of the deodorant include: extracts from leaves of Theaceae plants, which are cited as examples in U.S. Pat. No. 6,469,080 and WO 2003/104349; composite hydrous oxides of zinc-silicon or zinc-aluminum, which are cited as examples in the specification of Japanese Patent Application No. 280373/2003; and specific zeolite cited as examples in the specification of Japanese Patent Application No. 001778/2004. The amount of the deodorant being used is favorably in the range of 0.001 to 10 mass parts, more favorably 0.05 to 5 mass parts, particularly favorably 0.1 to 3 mass parts, per 100 mass parts of the water-absorbent resin. The case where the amount of the deodorant being added is smaller than 0.001 mass part has a possibility of resulting in failure to obtain the desired deodorization effect and is therefore not very favorable. On the other hand, the addition of the deodorant in an amount of larger than 10 mass parts has a merit of giving a material excellent in the deodorization effect, but greatly increases the price of the resultant water-absorbent resin composition itself and is therefore, in point of costs, not very favorable to the use of the resultant water-absorbent resin for disposable sanitary materials/absorbent articles (e.g. disposable diapers/sanitary napkins).

For the purpose of improving the handling easiness of the water-absorbent resin under a high humidity, it is also favorable to add thereto either a fine particulate silicon dioxide powder as the inorganic powder or a fine particulate polyvalent-metal stearate powder as the salt. The amount of these additives being used is favorably in the range of 0.01 to 10 mass parts, more favorably 0.05 to 5 mass parts, particularly favorably 0.1 to 1 mass part, per 100 mass parts of the water-absorbent resin. The case where the amount of the fine particulate silicon dioxide powder and/or fine particulate polyvalent-metal stearate powder being added is smaller than 0.01 mass part has a possibility of resulting in failure to obtain the desired effect of improving the handling easiness under a high humidity and is therefore not very favorable. On the other hand, the addition of the fine particulate silicon dioxide powder and/or fine particulate polyvalent-metal stearate powder in an amount of larger than 10 mass parts has a merit of giving a material excellent in the handling easiness under a high humidity, but greatly increases the price of the resultant water-absorbent resin composition itself and is therefore, in point of costs, not very favorable to the use of the resultant water-absorbent resin for disposable sanitary materials/absorbent articles (e.g. disposable diapers/sanitary napkins).

As to the water-absorbent resin in the present invention, the shape of its particles may be such an irregularly pulverized shape as obtained by the production process according to the present invention, but may be, for example, a shape as it is obtained by the reversed-phase suspension polymerization, namely, such as a spherical shape.

However, as to the reversed-phase suspension polymerization, the shape of the resultant water-absorbent resin is a spherical shape or a shape of its agglomerate and therefore often provides insufficient results with regard to mixing with or fixation to (hold on) pulp and is particularly unsuitable for recently trendy diapers containing water-absorbent resins in high concentrations. Thus, the shape of the water-absorbent resin according to the present invention is favorably an irregularly pulverized shape (i.e. a shape of a pulverized powder).

The water-absorbent resin obtained by the production process according to the present invention and the novel water-absorbent resin according to the present invention are usable for various uses of water-absorbent resins, for example, for sanitary materials, engineering works and building, solidification of waste liquids, agriculture and plants, and foods.

Incidentally, in the present invention, the absorbent article refers to a terminal consumer product which is a molding that contains a water-absorbent resin, and the absorbent article is represented by disposable diapers, sanitary napkins, and incontinent pads. Such an absorbent article favorably uses, for its molding, a fibrous material. As to the water-absorbent resin according to the present invention, if the mass ratio of the water-absorbent resin to the total of the water-absorbent resin and the fibrous material is favorably in the range of 20 to 100 mass %, more favorably 30 to 90 mass %, particularly favorably 30 to 60 mass %, and if the amount of the water-absorbent resin being used per one absorbent article is favorably in the range of 5 to 25 g, more favorably 8 to 15 g, then the water-absorbent resin can exercise the maximum effects in such an absorbent article. Furthermore, the more uniformly the water-absorbent resin according to the present invention and the fibrous material are mixed together (the less locally the water-absorbent resin is distributed), the more this resin can exercise the maximum effects in such an absorbent article.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to the below-mentioned Examples.

In the case where a commercially available water-absorbent resin (e.g. water-absorbent resin in a diaper) has already absorbed moisture in the distribution process, the measurement of the properties will do if it is carried out after the water-absorbent resin has been dried (e.g. dried under a reduced pressure at 60° C. for 16 hours) so as to reach an equilibrium water-containing state (where the water content is, for example, around 5 mass %).

Hereinafter, although detailed data are omitted, all the water-absorbent resins obtained in accordance with the present invention were substantially water-insoluble and had water contents of not higher than 7 mass % (solid contents of not lower than 93 mass %) and residual monomer contents of not higher than 400 mass ppm.

Incidentally, the performances of the water-absorbent resins and absorbent articles were measured by the following methods.

(a) Absorption Capacity without Load:

An amount of 0.2 g of water-absorbent resin was uniformly placed into a nonwoven-fabric-made bag (60 mm×80 mm) and then immersed into a 0.90 mass % aqueous sodium chloride solution (physiological saline solution) of which the temperature had been adjusted to 25° C. After 60 minutes, the bag was pulled up and then drained of water at 250 G with a centrifugal separator for 3 minutes, and then the mass $W_2$ (g) of the bag was measured. In addition, the same procedure as the above was carried out without the water-absorbent resin, and the resultant mass $W_1$ (g) was measured. Then, the absorption capacity (g/g) without load was calculated from these masses $W_1$ and $W_2$ in accordance with the following equation:

Absorption capacity(g/g)without load=((mass $W_2$(g)−mass $W_1$(g))/mass (g)of water-absorbent resin)−1

(b) Monolayer Absorption Capacity Under Load:

Onto a stainless metal gauze of 400 meshes (mesh opening size: 38 μm) at the bottom of a plastic supporting cylinder of 60 mm in inner diameter (wherein the metal gauze had been fused to one edge (bottom) of a cylindrical section of the supporting cylinder), there was uniformly spread 0.20 g of water-absorbent resin, and further thereon, there was mounted a piston (cover plate), wherein the piston had an outer diameter of only a little smaller than 60 mm and made no gap with the inner wall surface of the supporting cylinder, but was not hindered from moving up and down. Then, the total mass $W_3$ (g) of the supporting cylinder, the water-absorbent resin, and the piston was measured. On this piston, there was mounted a load as adjusted so that a load of 20 g/cm² (1.96 kPa) including the piston could uniformly be applied to the water-absorbent resin. Thereby one set of measurement apparatus had been completed. A glass filter plate of 90 mm in diameter was mounted inside a Petri dish of 150 mm in diameter, and then a 0.90 mass % aqueous sodium chloride solution (physiological saline solution) of 25° C. was added up to the same level as the upside of the glass filter plate, on which a filter paper of 9 cm in diameter (No. 2 of Toyo Filter Paper Co., Ltd.) was then mounted so that its entire surface would be wetted, and further, an excess of liquid was removed.

The above one set of measurement apparatus was mounted on the above wet filter paper, thereby allowing the water-absorbent resin to absorb the liquid under load. If the liquid surface went down from the upside of the glass filter plate, then the liquid was added to keep the liquid surface level on a constant level. Then, 1 hour later, the one set of measurement apparatus was removed by being lifted to re-measure the mass $W_4$ (g) excluding the load (total mass of the supporting cylinder, the swollen water-absorbent resin, and the piston).

Then, the monolayer absorption capacity (g/g) under load was calculated from these masses $W_3$ and $W_4$ in accordance with the following equation:

Monolayer absorption capacity(g/g)under load=(mass $W_4$(g)−mass $W_3$(g))/mass(g)of water-absorbent resin (c) Mass(weight)-Average Particle Diameter (D50):

Water-absorbent resins were classified with JIS standard sieves having mesh opening sizes of such as 850 μm, 600 μm, 500 μm, 425 μm, 300 μm, 212 μm, 150 μm, 106 μm, and 75 μm. Then, the percentages of the residues on these sieves were plotted on a logarithmic probability paper. Therefrom, the mass-average particle diameter (D50) was read.

As to the sieve classification, 10.00 g of water-absorbent resin powder or water-absorbent resin was placed onto JIS standard sieves (having mesh opening sizes of such as 850 μm, 600 μm, 500 μm, 425 μm, 300 μm, 212 μm, 150 μm, 106 μm, and 75 μm) (The IIDA TESTING SIEVE: inner diameter=80 mm) and then classified with a ROTAP type sieve shaker (ES-65 type sieve shaker produced by Iida Seisakusho K. K.) for 10 minutes. Incidentally, as described in such as U.S. Pat. No. 5,051,259, the mass-average particle diameter (D50) refers to the particle diameter of a standard sieve having a definite mesh opening size and corresponding to 50 mass % of the entire particles and, in the below-mentioned Examples, was calculated by use of JIS standard sieves having mesh opening sizes of 850 μm, 600 μm, 300 μm, and 150 μm.

(d) Absorption Efficiency Under Load:

The absorption capacity without load and monolayer absorption capacity under load of the water-absorbent resin were measured by the methods as mentioned in (a) and (b) above. Then, the absorption efficiency (%) under load was calculated in accordance with the following equation:

Absorption efficiency(%)under load=monolayer absorption capacity(g/g)under load×100/absorption capacity(g/g)without load (e) Total Absorption Capacity:

The absorption capacity without load and monolayer absorption capacity under load of the water-absorbent resin were measured by the methods as mentioned in (a) and (b) above. Then, the total absorption capacity (g/g) was calculated in accordance with the following equation:

Total absorption capacity(g/g)=monolayer absorption capacity(g/g)under load+absorption capacity(g/g) without load (f) Evaluation of Absorbent Article (Test for Wet-Back Amount):

The absorbent articles as obtained from the below-mentioned Examples and Comparative Examples were used. A load of 1.96 kPa was applied to the entirety of each absorbent article, and then they were left intact at room temperature. An amount of 75 g of a 0.90 mass % aqueous sodium chloride solution (physiological saline solution) as adjusted to 37° C. was injected into a central portion of the absorbent article through a cylinder of 70 mm in diameter and 100 mm in height. The absorbent article was left put under the load for 1 hour, and then the same operation was repeated. Then, 30 minutes later than the fourth-time injection of the physiological saline solution (total amount of physiological saline solution injected=300 g), the load was removed from the absorbent article, and then a paper towel (manufacturer: Oji Paper-Manufacturing Co., Ltd.; Kitchen Towel Extra-Dry, 30-ply as cut into the size of 120 mm×450 mm) was mounted on the absorbent article, and then a load of 37 g/cm² (3.63 kPa) was applied thereto for 1 minute to measure the amount of the liquid backing to the paper towel.

Production Example 1

A reaction liquid was prepared by dissolving 2.1 g of polyethylene glycol diacrylate (molar-number-average degree of addition polymerization of ethylene oxide: 8) into 5,500 g of an aqueous solution of sodium acrylate having a neutralization degree of 75 mol % (monomer concentration: 38 mass %). Next, dissolved oxygen was removed from this reaction liquid under a nitrogen gas atmosphere for 30 minutes. Next, the above reaction liquid was supplied to a reactor as prepared by lidding a jacketed stainless twin-arm kneader of 10 liters in capacity having two sigma-type blades. While the reaction liquid was kept at 30° C., air in the system was displaced with nitrogen gas. Subsequently, while the reaction liquid was stirred, 2.46 g of sodium persulfate and 0.10 g of L-ascorbic acid were added thereto. As a result, polymerization started after about 1 minute. Then, the polymerization was carried out in the range of 30 to 90° C., and the resultant hydrogel polymer was got out 60 minutes later than the start of the polymerization. The resultant hydrogel polymer was what had been divided into small pieces having diameters of about 5 mm. This hydrogel polymer having been divided into small pieces was spread onto a metal gauze of 50 meshes (mesh opening size: 300 μm) and then dried with hot air of 170° C. for 50 minutes. Next, the dried product was pulverized with a vibratory mill and then classified and regulated with a metal gauze of 20 meshes (mesh opening size: 850 μm), thus obtaining a water-absorbent resin powder (1) of an irregularly pulverized shape, which exhibited an absorption capacity of 57 (g/g) without load and had a mass-average particle diameter of 425 μm and included a powder having particle diameters of smaller than 150 μm in an amount of 2 mass % relative to the water-absorbent resin powder.

Production Example 2

A reaction liquid was prepared by dissolving 2.2 g of polyethylene glycol diacrylate (molar-number-average degree of addition polymerization of ethylene oxide: 8) into 5,500 g of an aqueous solution of sodium acrylate having a neutralization degree of 75 mol % (monomer concentration: 36 mass %). Next, dissolved oxygen was removed from this reaction liquid under a nitrogen gas atmosphere for 30 minutes. Next, the above reaction liquid was supplied to a reactor as prepared by lidding a jacketed stainless twin-arm kneader of 10 liters in capacity having two sigma-type blades. While the reaction liquid was kept at 30° C., air in the system was displaced with nitrogen gas. Subsequently, while the reaction liquid was stirred, 2.46 g of sodium persulfate and 0.10 g of L-ascorbic acid were added thereto. As a result, polymerization started after about 1 minute. Then, the polymerization was carried out in the range of 30 to 90° C., and the resultant hydrogel polymer was got out 60 minutes later than the start of the polymerization. The resultant hydrogel polymer was what had been divided into small pieces having diameters of about 5 mm. This hydrogel polymer having been divided into small pieces was spread onto a metal gauze of 50 meshes (mesh opening size: 300 μm) and then dried with hot air of 170° C. for 50 minutes. Next, the dried product was pulverized with a vibratory mill and then classified and regulated with a metal gauze of 20 meshes (mesh opening size: 850 μm), thus obtaining a water-absorbent resin powder (2) of an irregularly pulverized shape, which exhibited an absorption capacity of 56 (g/g) without load and had a mass-average particle diameter of 370 μm and included a powder having particle diameters of smaller than 150 μm in an amount of 5 mass % relative to the water-absorbent resin powder.

Example 1

An amount of 100 mass parts of the water-absorbent resin powder (1), having been obtained from Production Example 1 and having a powder temperature of 60° C., was mixed with a surface-crosslink-treating agent (having been prepared from 0.4 mass part of propylene glycol, 0.02 mass part of ethylene glycol diglycidyl ether, 0.25 mass part of 1,4-butanediol, and 2.5 mass parts of water) by Lödige Mixer. Then, 2 minutes later, the resultant mixture was placed into a heating treatment apparatus having an adjusted temperature of 195° C. and then heat-treated for 45 minutes, thus obtaining a water-absorbent resin (1).

Shown in Table 1 are the absorption capacity without load, monolayer absorption capacity under load, absorption efficiency under load, total absorption capacity, particle diameter distribution, and mass-average particle diameter of the resultant water-absorbent resin (1).

Example 2

An amount of 100 mass parts of the water-absorbent resin powder (2), having been obtained from Production Example 2 and having a powder temperature of 60° C., was mixed with a surface-crosslink-treating agent (having been prepared from 0.4 mass part of propylene glycol, 0.02 mass part of ethylene glycol diglycidyl ether, 0.25 mass part of 1,4-butanediol, and 2.5 mass parts of water) by Lödige Mixer. Then, 1 minute later, the resultant mixture was placed into a heating treatment apparatus having an adjusted temperature of 195° C. and then heat-treated for 45 minutes, thus obtaining a water-absorbent resin (2).

Shown in Table 1 are the absorption capacity without load, monolayer absorption capacity under load, absorption efficiency under load, total absorption capacity, particle diameter distribution, and mass-average particle diameter of the resultant water-absorbent resin (2).

Comparative Example 1

An amount of 100 mass parts of the water-absorbent resin powder (1), having been obtained from Production Example 1 and having a powder temperature of 60° C., was mixed with a surface-crosslink-treating agent (having been prepared from 0.4 mass part of propylene glycol, 0.02 mass part of ethylene glycol diglycidyl ether, 0.25 mass part of 1,4-butanediol, and 2.5 mass parts of water) by Lödige Mixer. Then, 1 hour later, the resultant mixture was placed into a heating treatment apparatus having an adjusted temperature of 195° C. and then heat-treated for 55 minutes, thus obtaining a comparative water-absorbent resin (1).

Shown in Table 1 are the absorption capacity without load, monolayer absorption capacity under load, absorption efficiency under load, total absorption capacity, particle diameter distribution, and mass-average particle diameter of the resultant comparative water-absorbent resin (1).

Comparative Example 2

An amount of 100 mass parts of the water-absorbent resin powder (2), having been obtained from Production Example 2 and having a powder temperature of 60° C., was mixed with a surface-crosslink-treating agent (having been prepared from 0.4 mass part of propylene glycol, 0.02 mass part of ethylene glycol diglycidyl ether, 0.25 mass part of 1,4-butanediol, and 2.5 mass parts of water) by Lödige Mixer. Then, 10 minutes later, the resultant mixture was placed into a heating treatment apparatus having an adjusted temperature of 195° C. and then heat-treated for 55 minutes, thus obtaining a comparative water-absorbent resin (2).

Shown in Table 1 are the absorption capacity without load, monolayer absorption capacity under load, absorption efficiency under load, total absorption capacity, particle diameter distribution, and mass-average particle diameter of the resultant comparative water-absorbent resin (2).

Comparative Example 3

An amount of 100 mass parts of the water-absorbent resin powder (2), having been obtained from Production Example 2 and having a powder temperature of 60° C., was mixed with a surface-crosslink-treating agent (having been prepared from 0.4 mass part of propylene glycol, 0.02 mass part of ethylene glycol diglycidyl ether, 0.25 mass part of 1,4-butanediol, and 2.5 mass parts of water) by Lödige Mixer. Then, 20 minutes later, the resultant mixture was placed into a heating treatment apparatus having an adjusted temperature of 195° C. and then heat-treated for 55 minutes, thus obtaining a comparative water-absorbent resin (3).

Shown in Table 1 are the absorption capacity without load, monolayer absorption capacity under load, absorption efficiency under load, total absorption capacity, particle diameter distribution, and mass-average particle diameter of the resultant comparative water-absorbent resin (3).

Example 3

An amount of 50 mass parts of the water-absorbent resin (1) (having been obtained from Example 1) and 50 mass parts of wood-pulverized pulp were mixed together by a mixer in a dry manner. Next, the resultant mixture was pneumatically molded on a wire screen (formed into 400 meshes (mesh opening size: 38 μm)) with a batch type pneumatic molding apparatus and thereby shaped into a web of a size of 120 mm×400 mm. Furthermore, this web was pressed by a pressure of 196.14 kPa for 5 seconds, thus obtaining an absorbent structure having a basis weight of about 0.05 g/cm$^2$.

Subsequently, so-called a back sheet made of liquid-impermeable polypropylene (liquid-impermeable sheet), the above absorbent structure, a surface sheet of a nonwoven fabric made of liquid-permeable polypropylene (liquid-permeable sheet) were stuck on each other in that order with a double-coated tape, thus obtaining a sanitary absorbent article (i.e. disposable diaper) (1). The mass of this absorbent article (1) was 45 g.

The resultant absorbent article (1) was tested for the wet-back amount. The result is shown in Table 2.

Example 4

An absorbent article (2) was obtained in the same way as of Example 3 except that the water-absorbent resin (1) was replaced with the water-absorbent resin (2) (having been obtained from Example 2).

The resultant absorbent article (2) was tested for the wet-back amount. The result is shown in Table 2.

Comparative examples 4 to 6

Comparative absorbent articles (1), (2), and (3) were obtained in the same way as of Example 3 except that the water-absorbent resin (1) was replaced with the comparative water-absorbent resins (1), (2), and (3) (having been obtained from Comparative Examples 1, 2, and 3).

The resultant comparative absorbent articles (1), (2), and (3) were tested for the wet-back amount. The results are shown in Table 2.

5,500 g of an aqueous solution of sodium acrylate having a neutralization degree of 75 mol % (monomer concentration: 38 mass %). Next, dissolved oxygen was removed from this reaction liquid in the same way as of Production Example 1 and then supplied to the same reactor as used in Production Example 1. While the reaction liquid was kept at 30° C., air in the system was displaced with nitrogen gas. Subsequently, while the reaction liquid was stirred, 2.98 g of sodium persulfate and 0.015 g of L-ascorbic acid were added thereto. As a result, polymerization started after about 1 minute. Then, the polymerization was carried out in the range of 25 to 90° C., and the resultant hydrogel polymer was got out 60 minutes later than the start of the polymerization. The resultant hydrogel polymer was what had been divided into particles having particle diameters of about 1 to about 5 mm. This hydrogel polymer was dried in the same way as of Production Example 1. Next, the dried product was pulverized with a roll mill and then classified with a metal gauze of 850 μm in mesh opening size and then further classified with a metal gauze of 150 μm in mesh opening size in order to remove a fine powder from the classified material, thus obtaining a water-absorbent resin

TABLE 1

| | | Absorption capacity (g/g) without load | Monolayer absorption capacity (g/g) under load | Absorption efficiency (%) under load | Total absorption capacity (g/g) | Particle diameter distribution (mass %) | | | | | Mass-average particle diameter (μm) |
|---|---|---|---|---|---|---|---|---|---|---|---|
| | | | | | | Not smaller than 850 μm | Smaller than 850 μm but not smaller than 600 μm | Smaller than 600 μm but not smaller than 300 μm | Smaller than 300 μm but not smaller than 150 μm | Smaller than 150 μm | |
| Example 1 | Water-absorbent resin (1) | 46 | 35 | 76 | 81 | 0 | 16 | 68 | 15 | 1 | 425 |
| Example 2 | Water-absorbent resin (2) | 46 | 36 | 78 | 82 | 0 | 15 | 52 | 28 | 3 | 370 |
| Comparative Example 1 | Comparative water-absorbent resin (1) | 47 | 24 | 51 | 71 | 0 | 16 | 68 | 15 | 1 | 425 |
| Comparative Example 2 | Comparative water-absorbent resin (2) | 45 | 29 | 64 | 74 | 0 | 15 | 52 | 28 | 3 | 370 |
| Comparative Example 3 | Comparative water-absorbent resin (3) | 43 | 29 | 67 | 72 | 0 | 15 | 52 | 28 | 3 | 370 |

TABLE 2

| | Water-absorbent resin used | Wet-back amount (g) |
|---|---|---|
| Example 3 | Water-absorbent resin (1) | 8 |
| Example 4 | Water-absorbent resin (2) | 7 |
| Comparative Example 4 | Comparative water-absorbent resin (1) | 14 |
| Comparative Example 5 | Comparative water-absorbent resin (2) | 18 |
| Comparative Example 6 | Comparative water-absorbent resin (3) | 16 |

Example 5

A reaction liquid was prepared by dissolving 2.5 g of polyethylene glycol diacrylate (molar-number-average degree of addition polymerization of ethylene oxide: 8) into powder (3) of an irregularly pulverized shape, which exhibited an absorption capacity of 55 g/g without load and had a mass-average particle diameter of about 420 μm and included a powder having particle diameters of smaller than 150 μm in an amount of 0.8 mass % relative to the water-absorbent resin powder.

Next, 100 mass parts of the water-absorbent resin powder (3), having been obtained in the above way and having a powder temperature of 60° C., was mixed with an aqueous surface-crosslinking agent solution (having been prepared from 0.5 mass part of propylene glycol, 0.02 mass part of ethylene glycol diglycidyl ether, 0.3 mass part of 1,4-butanediol, and 2.5 mass parts of water) by Lödige Mixer. Then, 1 minute later, the resultant mixture was placed into a heating treatment apparatus having an adjusted temperature of 195° C. and then heat-treated for 40 minutes, thus obtaining a water-absorbent resin (3).

Shown in Table 3 are the absorption capacity without load, monolayer absorption capacity under load, absorption efficiency under load, total absorption capacity, and mass-average particle diameter (D50) (determined by the classification with the JIS standard sieves having mesh opening sizes of 850 μm, 600 μm, 300 μm, and 150 μm) of the resultant water-absorbent resin (3). In addition shown in Table 4 is the logarithmic standard deviation (σζ) of the particle diameter distribution (determined by the classification with the JIS standard sieves having mesh opening sizes of 850 μm, 710 μm, 600 μm, 500 μm, 425 μm, 300 μm, 212 μm, 150 μm, and 45 μm) of the resultant water-absorbent resin (3).

Incidentally, in Table 4, there are also listed the particle diameter distributions and their logarithmic standard deviations (σζ) of the water-absorbent resins obtained from Examples 1 and 2 and Comparative Examples 1 to 3.

same conditions as of Example 3, thus obtaining an absorbent structure having a basis weight of about 0.04 g/cm².

Subsequently, an absorbent article (4) having a mass of 37 g was obtained in the same way as of Example 3.

The resultant absorbent article (4) was tested for the wet-back amount in the same way as of Example 3. As a result, the wet-back amount was 25 g.

TABLE 3

| | | Absorption capacity (g/g) without load | Monolayer absorption capacity (g/g) under load | Absorption efficiency (%) under load | Total absorption capacity (g/g) | Particle diameter distribution (mass %) | | | | | D50 (μm) |
|---|---|---|---|---|---|---|---|---|---|---|---|
| | | | | | | Not smaller than 850 μm | Smaller than 850 μm but not smaller than 600 μm | Smaller than 600 μm but not smaller than 300 μm | Smaller than 300 μm but not smaller than 150 μm | Smaller than 150 μm | |
| Example 5 | Water-absorbent resin (3) | 45 | 35 | 78 | 80 | 0.0 | 17.2 | 66.6 | 15.4 | 0.8 | 425 |

TABLE 4

| | | Particle diameter distribution (mass %) | | | | | | | | | | |
|---|---|---|---|---|---|---|---|---|---|---|---|---|
| | | Not smaller than 850 μm | Smaller than 850 μm but not smaller than 710 μm | Smaller than 710 μm but not smaller than 600 μm | Smaller than 600 μm but not smaller than 500 μm | Smaller than 500 μm but not smaller than 425 μm | Smaller than 425 μm but not smaller than 300 μm | Smaller than 300 μm but not smaller than 212 μm | Smaller than 212 μm but not smaller than 150 μm | Smaller than 150 μm but not smaller than 45 μm | Smaller than 45 μm | σζ |
| Example 1 | Water-absorbent resin (1) | 0.0 | 1.5 | 14.5 | 15.7 | 18.3 | 34.0 | 11.2 | 4.1 | 0.7 | 0.0 | 0.348 |
| Example 2 | Water-absorbent resin (2) | 0.0 | 1.2 | 14.2 | 12.8 | 15.5 | 24.1 | 19.3 | 9.1 | 3.2 | 0.2 | 0.482 |
| Comparative Example 1 | Comparative water-absorbent resin (1) | 0.0 | 1.5 | 14.5 | 15.7 | 18.3 | 34.0 | 11.2 | 4.1 | 0.7 | 0.0 | 0.348 |
| Comparative Example 2 | Comparative water-absorbent resin (2) | 0.0 | 1.2 | 14.2 | 12.8 | 15.5 | 24.1 | 19.3 | 9.1 | 3.2 | 0.2 | 0.482 |
| Comparative Example 3 | Comparative water-absorbent resin (3) | 0.0 | 1.2 | 14.2 | 12.8 | 15.5 | 24.1 | 19.3 | 9.1 | 3.2 | 0.2 | 0.482 |
| Example 5 | Water-absorbent resin (3) | 0.0 | 5.2 | 12.0 | 25.6 | 16.4 | 24.6 | 11.7 | 3.7 | 0.8 | 0.0 | 0.357 |

Example 6

An absorbent article (3) was obtained in the same way as of Example 3 except that the water-absorbent resin (1) was replaced with the water-absorbent resin (3) (having been obtained from Example 5).

The resultant absorbent article (3) was tested for the wet-back amount in the same way as of Example 3. As a result, the wet-back amount was 8 g.

Example 7

An amount of 35 mass parts of the water-absorbent resin (3) (having been obtained from Example 5) and 65 mass parts of wood-pulverized pulp were mixed together by a mixer in a dry manner. Next, the resultant mixture was shaped into a web of a size of 120 mm×400 mm with the same apparatus as used in Example 3. Furthermore, this web was pressed under the Comparative Example 7

A comparative absorbent article (4) was obtained in the same way as of Example 7 except that the water-absorbent resin (3) was replaced with the comparative water-absorbent resin (1) (having been obtained from Comparative Example 1).

The resultant comparative absorbent article (4) was tested for the wet-back amount in the same way as of Example 3. As a result, the wet-back amount was 39 g.

INDUSTRIAL APPLICATION

The water-absorbent resin in the present invention has excellent absorption properties and therefore can be utilized for a wide range of uses. Particularly, because the water-absorbent resin obtained by the production process according to the present invention involves using no hydrophilic organic solvent in the surface-crosslinking treatment, this resin is favorable for sanitary materials/absorbent articles (e.g. disposable diapers/sanitary napkins) and can be used favorably for the sanitary materials by being combined with hydrophilic fibrous materials (e.g. pulverized pulp).

The invention claimed is:

1. A water-absorbent resin, which is a water-absorbent resin comprising sodium polyacrylate obtained by a process including the step of polymerizing and crosslinking a monomer component including acrylic acid and/or its sodium salt (neutralized material) as a main component, wherein the water-absorbent resin has a mass-average particle diameter of 380 to 550 μm; includes a powder having particle diameters of smaller than 150 μm in an amount of 0 to 3 mass % relative to the water-absorbent resin; and includes a powder having particles of not smaller than 300 μm comprising not less than 60 mass % of the entirety of the water-absorbent resin; has an uncrosslinked water-extractable component content (water-soluble polymer content) of 0 to 25 mass % relative to the water-absorbent resin, and exhibits an absorption capacity of not less than 35 g/g without load, a total absorption capacity of not less than 70 (g/g) and an absorption efficiency of not less than 70% under load, wherein the total absorption capacity and the absorption efficiency under load are defined by the following equations based on values given by absorption of a 0.90 mass % aqueous sodium chloride solution (25° C.) for 1 hour:

total absorption capacity(g/g)=absorption capacity(g/g)without load+monolayer absorption capacity(g/g)under load; and absorption efficiency(%)under load=monolayer absorption capacity(g/g)under load×100/absorption capacity(g/g)without load.

2. A water-absorbent resin according to claim 1, wherein the particles have an irregularly pulverized shape.

3. An absorbent article for absorption of excreta and blood, which comprises the water-absorbent resin as recited in claim 1.

4. A water-absorbent resin according to claim 1, which exhibits an absorption capacity of not less than 40 g/g without load.

5. A water-absorbent resin according to claim 1, which has a particle size such that: particles of smaller than 850 μm but not smaller than 150 μm comprise not less than 90 mass % of the entirety.

6. A water-absorbent resin according to claim 1, which has a residual monomer content of 0 to 400 mass ppm.

7. A water-absorbent resin according to claim 1, which includes an inorganic powder in an amount of 0.01 to 10 mass parts per 100 mass parts of the water-absorbent resin.

8. A water-absorbent resin according to claim 1, which includes a deodorant in an amount of 0.001 to 10 mass parts per 100 mass parts of the water-absorbent resin.

9. A water-absorbent resin according to claim 1, which exhibits a total absorption capacity of not less than 78 g/g.

10. An absorbent article comprising the water-absorbent resin according to claim 1, which further comprises a fibrous material, wherein the mass ratio of the water-absorbent resin to the total of the water-absorbent resin and the fibrous material is in the range of 20 to 100 mass %, and the amount of the water-absorbent resin per one absorbent article is in the range of 5 to 25 g.

11. A water-absorbent resin according to claim 1, wherein the sodium polyacrylate has a neutralization degree of 50 to 90 mol %.

12. A water-absorbent resin according to claim 11, wherein the sodium polyacrylate has a neutralization degree of 60 to 80 mol %.

13. A water-absorbent resin according to claim 1, which has an uncrosslinked water-extractable component content (water-soluble polymer content) of 0 to 10 mass % relative to the water-absorbent resin.

14. A water-absorbent resin according to claim 7, wherein the inorganic powder is a fine particulate silicon dioxide powder.

15. A water-absorbent resin according to claim 1, which has an uncrosslinked water-extractable component content (water-soluble polymer content) of 0 to 20 mass % relative to the water-absorbent resin.

16. A water-absorbent resin according to claim 1, which has an uncrosslinked water-extractable component content (water-soluble polymer content) of 0 to 15 mass % relative to the water-absorbent resin.

17. A water-absorbent resin according to claim 1, which further comprises a fine particulate polyvalent-metal stearate powder in an amount of 0.01 to 10 mass parts per 100 mass parts of the water-absorbent resin.

18. The water-absorbent resin of claim 1 which is a water-absorbent resin comprising sodium polyacrylate obtained by a process including the step of polymerizing and crosslinking a monomer component including acrylic acid and/or its sodium salt (neutralized material) as a main component, wherein the water-absorbent resin has a mass-average particle diameter of 380 to 550 μm; includes a powder having particle diameters of smaller than 150 μm in an amount of 0 to 3 mass % relative to the water-absorbent resin; and includes a powder having particles of not smaller than 300 μm comprising not less than 60 mass % of the entirety of the water-absorbent resin; has an uncrosslinked water-extractable component content (water-soluble polymer content) of 0 to 25 mass % relative to the water-absorbent resin; and exhibits an absorption capacity of not less than 35 g/g without load, a total absorption capacity of not less than 70 (g/g) and an absorption efficiency of not less than 70% under load, wherein the total absorption capacity and the absorption efficiency under load are defined by the following equations based on values given by absorption of a 0.90 mass % aqueous sodium chloride solution (25° C.) for 1 hour:

total absorption capacity(g/g)=absorption capacity(g/g)without load+monolayer absorption capacity(g/g)under load;

absorption efficiency(%)under load=monolayer absorption capacity(g/g)under load×100/absorption capacity(g/g)without load; and a logarithmic standard deviation σζ of particle diameter distribution in the range of 0.25 to 0.50, wherein the logarithmic standard deviation σζ is defined by the following mathematical expression:

$$\sigma\zeta = 0.5 \times \ln(X_2/X_1)$$

where: $X_1$ denotes a particle diameter when R=84.1 mass % obtained by a process including the steps of classifying the water-absorbent resin with JIS standard sieves having mesh opening sizes of 850 μm, 710 μm, 600 μm, 500 μm, 425 μm, 300 μm, 212 μm, 150 μm, and 45 μm and then plotting the percentages R of the residues on a logarithmic probability paper; and $X_2$ denotes a particle diameter when R=15.9 mass % determined by the same method as $X_1$.

19. A water-absorbent resin according to claim 18, which has a particle size such that: particles of smaller than 850 μm but not smaller than 150 μm comprise not less than 90 mass % of the entirety.

20. A water-absorbent resin according to claim 18, which has a residual monomer content of 0 to 400 mass ppm.

21. A water-absorbent resin according to claim 18, which includes an inorganic powder in an amount of 0.01 to 10 mass parts per 100 mass parts of the water-absorbent resin.

22. A water-absorbent resin according to claim 18, which includes a deodorant in an amount of 0.001 to 10 mass parts per 100 mass parts of the water-absorbent resin.

23. A water-absorbent resin according to claim 21, wherein the inorganic powder is a fine particulate silicon dioxide powder.

24. A water-absorbent resin according to claim 18, which has an uncrosslinked water-extractable component content (water-soluble polymer content) of 0 to 20 mass % relative to the water-absorbent resin.

25. A water-absorbent resin according to claim 18, which has an uncrosslinked water-extractable component content (water-soluble polymer content) of 0 to 15 mass % relative to the water-absorbent resin.

26. A water-absorbent resin according to claim 18, which has an uncrosslinked water-extractable component content (water-soluble polymer content) of 0 to 10 mass % relative to the water-absorbent resin.

27. A water-absorbent resin according to claim 18, which further comprises a fine particulate polyvalent-metal stearate powder in an amount of 0.01 to 10 mass parts per 100 mass parts of the water-absorbent resin.

28. A process for production of the water-absorbent resin of claim 1, which comprises:
- a step (1) of polymerizing an aqueous solution of a monomer component including acrylic acid and/or its salt as a main component and another monomer in an amount of 0 to 30 mol % relative to the total of the main component, thereby obtaining a hydrogel polymer;
- a step (2) of drying and pulverizing the resultant hydrogel polymer to thereby obtain a water-absorbent resin powder;
- a step (3) of adding a surface-crosslink-treating agent to the resultant water-absorbent resin powder in a mixer, wherein the water-absorbent resin powder has a temperature in the range of 40 to 80° C. when the surface-crosslinking agent is added, a mass-average particle diameter of 380 to 550 µm and includes a powder having particle diameters of smaller than 150 µm in an amount of 0 to 3 mass % relative to the water-absorbent resin powder and wherein the surface-crosslink-treating agent includes a surface-crosslinking agent and water as essential components and has a hydrophilic organic solvent content of 0 to 10 mass % relative to the surface-crosslink-treating agent; and
- a step (4) of heating the resultant mixture in a heater to thereby carry out surface-crosslinking treatment;
- wherein a transfer time from the mixer from the end of the step (3) till introducing the mixture to the heater at the beginning of the step (4) is greater than 0 second and within 5 minutes, wherein the time of from the end of the step (3) till the beginning of the step (4) is a powder migration time from an outlet of the mixer to an inlet of the heater.

29. A process for production of a water-absorbent resin according to claim 28, wherein the water-absorbent resin powder obtained in the step (2) exhibits an absorption capacity of not less than 40 g/g without load.

30. A process for production of a water-absorbent resin according to claim 28, wherein the surface-crosslinking agent includes a polyhydric alcohol compound and wherein the amount of water in the surface-crosslink-treating agent is in the range of 0.5 to 20 mass % relative to the water-absorbent resin powder.

31. A process for production of a water-absorbent resin according to claim 29, wherein the surface-crosslinking agent includes a polyhydric alcohol compound and wherein the amount of water in the surface-crosslink-treating agent is in the range of 0.5 to 20 mass % relative to the water-absorbent resin powder.

32. A process for production of a water-absorbent resin according to claim 28, wherein the hydrophilic organic solvent has a boiling point of 50 to 170° C. and a solubility of not less than 1 g in 100 g of water of normal temperature.

* * * * *